United States Patent [19]
Siegel et al.

[11] Patent Number: 4,898,679
[45] Date of Patent: Feb. 6, 1990

[54] METHOD AND APPARATUS FOR OBTAINING OZONE SATURATED WATER

[76] Inventors: Seymour Siegel, Feeks La., Mill Neck, N.Y. 11765; Louis Maggio, 20 Woodoak Dr., Westbury, N.Y. 11590

[21] Appl. No.: 305,440

[22] Filed: Feb. 1, 1989

[51] Int. Cl.$^4$ ............................................. C02F 1/78
[52] U.S. Cl. ................................. 210/752; 210/740; 210/742; 210/744; 210/760; 210/765; 210/104; 210/149; 210/195.1; 210/221.1
[58] Field of Search ............... 210/104, 149, 177, 199, 210/195.1, 220, 188, 221.1, 221.2, 740, 742, 744, 752, 760, 765, 766; 422/28

[56] References Cited

U.S. PATENT DOCUMENTS

| | | | |
|---|---|---|---|
| 3,920,550 | 11/1975 | Farrell et al. | 210/104 X |
| 4,138,724 | 2/1979 | Kawauchi et al. | 210/760 X |
| 4,256,574 | 3/1981 | Bhorgava | 210/760 X |

*Primary Examiner*—Charles Hart
*Attorney, Agent, or Firm*—Bauer & Schaffer

[57] ABSTRACT

Gaseous ozone is admixed and stored with water under such conditions that the density of ozone in the water is increased above the normally obtained and held stably at such levels so that it may be efficiently transported through the processing plant being cleaned. Specifically, the present invention provides for the chilling of the ozone and water carrier to increase density and permit the subsequent increase in temperature to cause propulsion of the water and ozone through the plant to be cleaned in-place.

18 Claims, 1 Drawing Sheet

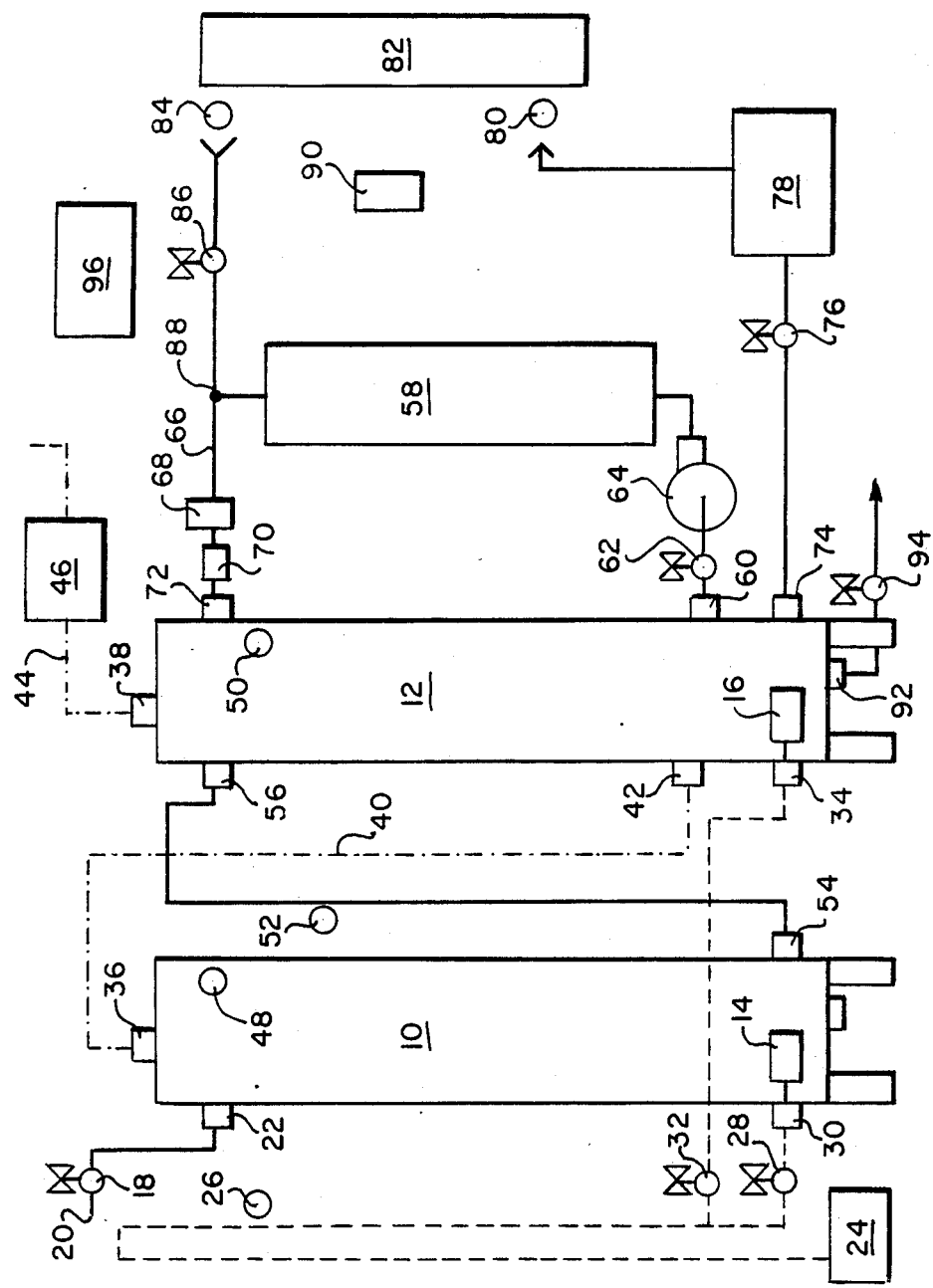

METHOD AND APPARATUS FOR OBTAINING OZONE SATURATED WATER

BACKGROUND OF THE INVENTION

The present invention relates to a system and apparatus for providing for the ozone cleansing and sanitation of parts, equipment and processing plants employed to process food or other organic material and more particularly, to a clean-in-place system and apparatus for sanitizing in-line equipment employed to process fluid material in which the equipment is normally cleaned by fluid washing and rinsing in a through-put similar to that used for the processed medium.

Clean-in-place systems are employed in a wide variety of industrial installations, and particularly in food processing plants to clean flow through pipes, storage tanks, cooking vessels and the like. These systems are referred to as clean-in-place systems because systems are cleaned by the passage of cleansing fluids loaded with soaps, detergents, etc., without dismantling the equipment or processing plant.

Cleaning is generally accomplished by breaking the processing plant down, removing small parts and exposing the larger parts to access. The small parts are cleansed separately while the larger in-situ parts are cleansed by first circulating water through the system as a first rinse. Then, cleaning chemicals are heated and circulated through the system to clean any remaining dirt out of the pipes or equipment. Next, the system is generally rinsed until "clean".

The use of ozone as a sanitizer is disclosed in "Ozone, The Process Water Steriliant" by Carl and Theresa Nebel, Pharmaceutical Manufacturing, April, 1984; Ozone Reduces Drying Odors 75–100% Joran, Russ et al, Food Processing, vol. 42, p. 44(1), Feb., 1981; Comparative Assessment of Chlorine, Heni, Ozone, and UV Light for Killing Legionella pneumophilia within a Model Plumbing System, Muvaca, et al, Applied And Environmental Microbiology, Feb, 1987 pp. 447–453; vol. 53, No. 2; Effect of Ozone on Bacterial Flora in Poultry During Refrigerated Storage, Nieto, J.C. et al., Int. Journal Refrigeration, 1984, vol. 7, No. 6, pp. 389,392; Stability of Ozone and its Germicidal Properties on Poultry Meat Microorganisms in Liquid Ozone, Yang, P.P.W. et al., Journal of Food Science, vol. 44(2) March/April, 1979, pp0. 501–504; Ozone Inactivation of Bacillus and Clastridium Spore Population and the Importance of Spore Cost to Resistance, Food Microbiology, Apr., 1985, vol. 2(2), pp. 123–134.

U.S. Pat. 4,409,188 deals with a device for sterilization of containers with ozone and U.S. Pat. 509,163 discloses a process for liberating ozone. Other patents employing ozone as sanitizing agents include U.S. Pat. 1,180,372; 3,549,528; 4,273,660; 4,549,477 and 4,655,932.

In spite of the subject matter of the above-identified patents and articles, there still exists a need for the provision of an improved sanitiing system or method and apparatus for accomplishing the same result in an efficient yet simple manner.

For example, among the problems inherent in the use of ozone is the fact that it is a gas and as such, it is highly volitile dissipating and evaporating under normal conditions, and in use, requires pressurization and enclosed, sealed chambers, to provide sufficient flow and density to be effective as a bactericide. These difficulties are exacerbated then attempting to cleanse elongated processing equipment which must first be washed with hot soapy water and rinsed thereafter with warm water.

It is the object of the present invention to provide a system for cleansing long or large processing plants using ozone sterilization, in which the problems and disadvantages enumerated above are overcome.

It is another object of the present invention to provide a system and apparatus for employing ozone as a sanitizing agent in which the handling of the ozone is provided simply, efficiently and economically.

It is yet another object of the present invention in which an ozone sanitizing system is provided which can be adapted for various clean-in-place manufacturing, processing and even disposal systems.

The foregoing objects and advantages, as well as others, will be apparent from the following disclosure of the present invention.

SUMMARY OF THE INVENTION

Briefly, the present invention provides a system and apparatus in which gaseous ozone is admixed and stored with water under such conditions that the density of ozone in the water is increased above that normally obtained, and held stabily at such levels, so that it may be efficiently transported through the processing plant being cleaned.

Specifically, the present invention provides for the chilling of the ozone and water carrier to increase density and when warmed, permit the subsequent increase in temperature to cause propulsion of the water and ozone through the plant to be cleaned-in-place.

A continuous loop is preferably provided, returning the ozone laden water to the first zone for replenishment, although in most instances, this may not be systemically or economically feasible. Disposal of the ozone laden water, itself pure, free of toxins, etc., can be made in any convenient manner, since once the ozone is exposed to atmosphere, it readily dissipates creating no hazard whatsoever.

BRIEF STATEMENT OF THE INVENTION

In particular, the process comprises introducing water into a first zone, bubbling ozone into the water for a time sufficient to substantially kill all bacteria present in the water and form an ozone demand-free water, passing the ozone demand-free water from the first zone to a second zone, bubbling ozone into the ozone demand-free water in the second zone, while passing the ozone demand-free water from the second zone into a chilling zone, chilling the ozone demand-free water in the chilling zone, returning the chilled ozone demand-free water to the second zone while continuously adding ozone thereto in the second zone and increasing the ozone in the chilled ozone demand-free water to a specific excess amount, and circulating the chilled ozone demand-free water containing the specific excess amount through the clean-in-place system, releasing excess ozone from the chilled ozone demand-free water and sanitizing the system, and returning ozone demand-free water to the first zone from the in-place system.

In addition to the sanitation of clean-in-place processing equipment, the present invention may provide ozone for the sanitizing of loose or separate parts or small equipment contained in a cleansing vessel or the like, or even for cleansing refuse garbage or sludge wherein contact with the carrier water poses no problem.

Another application may be found in the use of the ozone in the formation of ice, in block or particle form, which ice may then be used as a packing or storage material for fresh or processed foods. As the ice melts, the ozone is released to sterilize and purify the food, etc.

Still further, in accordance with the present invention, there is provided apparatus for producing an ozone saturated fluid, which may be employed in sanitizing an in-place system employed to process fluent material comprising a first container means for holding water, ozone bubbling means connected to the first container means for introducing ozone into water in the first container means, a second container means for holding ozone demand-free water from the first container means, means connecting the first container means with the second container means to pass ozone demand-free water from the first container means to the second container means, means connecting the ozone bubbling means to the second container means, and chilling container means connected to the second container means for receiving ozone demand-free water from the second container means, means connected to the chilling container means and to the second container means for returning chilled ozone demand-free water to the second container means, means for circulating the ozone demand-free water containing a specific excess amount of ozone from the second container means through the clean-in-place system on to other use and means connecting the in-place system or other use and the second container means to each other for return of ozone demand-free water from the in-place system or other use to the second container means.

Full details of the present invention are set forth in the following description and illustrated in the accompanying drawing.

BRIEF DESCRIPTION OF THE DRAWING

The figure is a diagrammatic flow sheet illustrating the sanitizing system, method and apparatus according to the invention.

DESCRIPTION OF THE PREFERRED EMBODIMENTS

As mentioned above, the effectiveness of ozone as a bacteria or virus killing agent is well known. However, in accordance with the present invention, the system, method and apparatus, condenses the ozone into demand-free water, that is water that has been previously sanitized with ozone. The concentration level is raised to above 2 ppm in the water through the use of a chiller. When the water is then led out into a clean-in-place system or in sludge treatment, the warmer pipes will result in a release of the ozone from the water and will provide for a more effective kill than that exhibited by normal sanitizing solutions. The half life of ozone in water is measured in minutes which means that there will be no residual chemicals that can get into the product and out to the consumer to any great extent to the nearby environment. Moreover, as the water is circulated around the clean-in-place system, ozone is reintroduced into the water, thus maintaining the concentration levels necessary to effectively kill any bacteria or other microorganisms and the like.

Referring more particularly to the figure, the system comprises pair of stainless steel tanks 10 and 12. These tanks 10 and 12 may vary in size and may, if desired, be made of any other suitable material such as metal with glass linings or of a metal other than stainless steel. In this regard, it is to be understood that the tanks may be made of any material which will not adversely react with ozone.

A ceramic diffuser 14 is disposed adjacent the bottom of tank 10 and serves as an inlet thereto. A like diffuser 16 is disposed simultaneously in tank 12. Diffusers 14 and 16 are designed to generate bubbles of 50 microns or less diameter.

A water fill solenoid valve 18 is located near the upper end of the tank 10 and is connected in a line 20 running to a source of water (not shown) and an inlet port 22 to the tank 10. A source of ozone 24 such as a cylinder of compressed ozone gas is connected, via a loop 26 and a solenoid valve 28 to an inlet 30 connected to diffuser 14 of tank 10. A second ozone solenoid valve 30 is disposed in parallel connecting the ozone loop 26 with the diffuser 16 in tank 12 via an inlet 34.

Tanks 10 and 12 are provided with vents 36 and 38 respectively, through which air and/or ozone may pass via line 40 and inlet 42 from tank 10 to tank 12 and via line 44 from the second tank 12 to the ozone kill unit 46, wherein the ozone is freed from any air.

Both tanks 10 and 12 are provided with level sensors 48 and 50 respectively, are kept filled by transferring ozone demand-free water from tank 10 through demand-free water outlet 52 to tank 12 through tank water fill inlet 56.

A chiller or chilling heat exchanger 58 is located downstream from tank 12, and is connected thereto via outlet 60, circulating valve 62 and pump 64 located near the lower portion of that tank. The chiller 58 is connected, by a return loop 66, to the tank 12 via an ozone detector 68, sampling the density of the ozone in the chilled water, a temperature valve 70, and an inlet valve 72. In this manner, continual circulation of chilled ozonated water is circulated into and fills the second tank 12.

An outlet 74, at the bottom of tank 12, is connected to a solenoid valve 76, permits the chilled water in tank 12 to pass through a heater 78 to the inlet 78 of the work site or user processing plant to be cleaned 82. The outlet of the water 82 is connected at 84. A return solenoid valve 86 is disposed by a tee fitting 88 to return line 66 to tank 12. The valve 86 permits water to flow from user 82 back into the system for re-use.

An ozone detector 90 which samples ambient air in the room where the apparatus is located, is disposed conveniently with respect to the apparatus as an environmental safety feature.

A drain 92 and solenoid operated valve 94 are provided to allow drainage of the second tank 12, when necessary, and finally, a control panel 96 is conveniently integrated into the system in accordance with known procedures so that the apparatus (i.e. valves, sensors, and the like), can be automatically and continuously program operated, or, if desirable, manually operated.

DETAILED OPERATIONAL SEQUENCE

Assuming the two tanks 10 and 12 are empty and the clean-in-place user is turned on. The clean-in-place processor or parts, etc. are, of course, cleansed with the usual soap and water cleaning processes. All solenoid valves and peripheral equipment are off. The system is now activated.

The level sensor 48 at the top of the demand-free tank 10 will cause the control panel 96 to energize the water fill solenoid 18. The water will then flow into the demand-free tank 10 through the water fill inlet 22. When the level of the water in the demand-free tank 10 reaches the height of the level control 48, the control panel 96 will de-energize the water fill solenoid 18 stopping the flow of water.

Once the demand-free tank 10 is filled with water, the ozone generator 24 will be activated, and ozone gas solenoid valve 28 opened allowing the ozone gas to flow through the ozone loop 26, then through the tank ozone inlet 30 and finally, through the ozone ceramic diffuser 14 into tank 10.

The ozone ceramic diffuser 14 creates a stream of microbubbles of ozone (50 microns or less in diameter) that rise up through the water in the demand-free tank 10. The action of the ozone as it rises through the water is to kill any bacteria in the water within tank 10 resulting in water substantially saturated with demand-free ozone. Any ozone remaining at the top of tank 10 will escape through vent tank 36 into the water tank 12, entering at the vented ozone inlet 42. The ozone will exit tank 12 to atmosphere through the vent 38 and the ozone kill unit 40. The ozone kill unit 40 will remove any remaining ozone from the effluent of tank 12 before it discharges to atmosphere.

Passing the excess ozone through the empty second water tank 12 will aid in sterilizing that vessel prior to filling it with water. Ozone is allowed to continue to bubble through the tanks 10 and 12 for at least a 30 minute period. When the 30 minute period has elapsed, control panel 96 is activated to re-energize the water fill solenoid valve 18 allowing water to flow into the tank 10 until water is caused to rise over the level in the tank 10 above the height of the filling loop 52. Once the water level is above the sensor 48, water will flow through the outlet 54, loop 52, through the fill inlet 28 into the second tank 12. When the control panel 96 receives an input from level sensor 56 indicating that the tank 12 is full, the water fill solenoid 18 is de-energized, stopping the flow of water, and the water in both tanks 10 and 12 levels out.

The second gas solenoid 32 is energized by the control panel 96 allowing ozone to flow into the ceramic diffuser 16 in the second tank 12, The first gas solenoid 28 is then de-energized stopping the flow of ozone gas into the tank 10.

The control panel 96 energizes the chilling loop circulating solenoid valve 62 and starts the chilling loop circulating pump 64. The ozone saturated water is now pumped from the tank 12 through the outlet 32, through the chiller 58 and back to the 12 through the return inlet 70. The water will be chilled to a temperature between 32 to 38 degrees Farenheit, preferably to at least 35 degrees Farenheit by circulating through the chiller 58, the temperature being sensed by sensor 70 and be continuously ozonated by the ceramic diffuser 16 located in the second tank 12, to its saturated level.

The ozone concentration or density is sensed by the ozone detector 68 which samples the return water from the chiller. When the concentration reaches the correct preselected or predetermined level, the control panel 96 will now allow the system to use the ozonated water for sterilization, by permitting flow out of tank 12 via the outlet 74.

When the system tells the control panel 96 that it is time for the sanitizing cycle, the chiller or chilling heat exchanger 58 is stopped and after 2 minutes, even the chilling loop circulating pump 64 is shut off and the chilling loop circulating solenoid valve 62 is de-energized stopping all flow of water.

The supply solenoid valve 76 leading to the user and the return solenoid valve 86 are energized effectively connecting those lines in parallel across the circulating pump 64 and the existing return line tee 88, thereby providing ozonated water to the user 82.

Normally, the existing sanitary pipes and equipment in the user 82 still warm from the previous use or cleaning cycle, so when the ozonated water comes in contact with the surfaces of the pipes and equipment of the user 82, the warming of the water causes a quick release of ozone aiding in the sterilizing process. The quick release of the ozone volitilizes the ozone, in situ, where its effect is most efficient and immediate. The ozone detector 68 samples the return water, monitors the concentration of the ozone in the return water and keeps a record in the control panel 96. If there is not enough release of the ozone, the water heater 78 may be energized by the control panel 96.

The maximum concentration of ozone allowable in the air is regulated by appropriate government authorities. The ozone detector 90 will inform the control panel 34 when the allowable limit, by parts per million or the like, is exceeded, and an alarm will sound, and a total system shutdown will occur.

OTHER APPLICATIONS

It has been noted that many applications can be made of the present invention, as for example:

In the treatment of sludge containing oxidizable, hazardous and toxic materials and stabilizable pathogens and microorganisms therein, the user 82 can be a sludge treatment zone such as a sludge sump, disposal barge, or piping system for carrying and dumping sludge. The ozone demand-free water containing the specific excess amount of ozone is released into the sludge treatment zone so as to be in direct contact with the sludge for a time sufficient to release the excess ozone therefrom and cause the organic toxic materials, pathogens and microorganisms to oxidize. The ozone demand-free water may thereafter be filtered and returned from the treatment zone to the first zone and the treated sludge recovered from the treatment zone for use or disposal as desired. In sea dumping, contact of ozone and sludge can be made by injecting the sludge with the ozone and water carrier, and/or using the ozone and water carrier as the carrier vehicle for the sludge. Of course, the ozone may also be disposed along with the waste sludge. Recovered sludge would be excellent organic fertilizer since it would no longer be toxic or waste.

In use as an ice component, the chilled ozonated water, which is approximately at freezing when passed into the user 82, can be directly mixed with pure water and frozen. The user 82 can thus be replaced with an ice making machine of conventional variety by which chip, flake, or even block ice can be formed. The ozonated water can be mixed in valve 80 or by separate manifold valving and directly passed over the freezing coils of the ice making machine. The ice thus formed can be used to pack fresh foods such as fish, seafood, meats, and the like for storage and transportation. It may be used also to pack processed foods in containers, cans, or the like.

During storage and/or transport the ice melts, and over extended periods the ozone is released to come into contact with and envelop the food or its containers. Foods will remain fresher over longer periods of time. The ozone is inert and volitilizes rapidly and, therefore, is not a hazard to the ultimate consumer of the food.

Since various modifications, changes and embodiments have been detailed and suggested herein, and others will be obvious to those skilled in the art, it is to be understood that the present invention is to be taken as illustrative and not as limiting of the present invention.

What is claimed is:

1. A method for obtaining ozone saturated water comprising introducing water into a first zone, bubbling ozone into the water in said first zone for a time sufficient to kill substantially all bacteria present in said water and form ozone demand-free water, passing the ozone demand-free water from said first zone to a second zone, bubbling ozone into said ozone demand-free water in said second zone while passing said ozone demand-free water from said second zone into a chilling zone, chilling said ozone demand-free water in said chilling zone, returning the chilled ozone demand-free water to said second zone while continuously adding ozone thereto in said second zone and increasing the ozone in said chilled ozone demand-free water to a specific excess amount until said chilled ozone reaches a temperature of between 32 to 38 degrees Farenheit.

2. The method according to claim 1 wherein the ozone bubbles, bubbled into the water in the first and second ozones, are microbubbles which are 50 microns or less in diameter.

3. The method according to claim 1 wherein any excess ozone in the first zone is passed into the second zone before ozone demand-free water is introduced into said second zone from said first zone.

4. The method according to claim 4 wherein the ozone introduced into the second zone is vented therefrom to the atmosphere after it is neutralized.

5. The method according to claim 6 wherein the ozone demand-free water is chilled to approximately 35 degrees Farenheit in the chilling zone.

6. A method for sanitizing an in-place system employed to process fluent material comprising introducing water into a first zone, bubbling ozone into the water in said first zone for a time sufficient to kill substantially all bacteria present in said water and form ozone demand-free water, passing the ozone demand-free water from said first zone to a second zone, bubbling ozone into said ozone demand-free water in said second zone while passing said ozone demand-free water from said second zone into a chilling zone, chilling said ozone demand-free water in said chilling zone, returning the chilled ozone demand-free water to said second zone while continuously adding ozone thereto in said second zone and increasing the ozone in said chilled ozone demand-free water to a specific excess amount, and circulating the chilled ozone demand-free water containing said specific excess amount through said in-place system, releasing excess ozone from said chilled ozone demand-free water and sanitizing said system, and returning ozone demand-free water to said first ozone from said in-place system.

7. The method according to claim 6 wherein the ozone bubbles, bubbled into the water in the first and second ozones, are microbubbles which are 50 microns or less in diameter.

8. The method according to claim 6 wherein the ozone demand-free water is chilled to approximately 35 degrees Farenheit in the chilling zone.

9. The method according to claim 8 wherein the chilled ozone demand-free water containing a specific excess amount of ozone from the second zone is heated before it is circulated to the in-place system, increasing its volitility.

10. A method for treating sludge containing ozidizable hazardous and toxic materials and stabilizable pathogens and microorganisms therein, comprising introducing water into a first zone, bubbling ozone into the water in said first zone for a time sufficient to kill substantially all bacteria present in said water and form ozone demand-free water, passing the ozone demand-free water from said first zone to a second zone, bubbling ozone into said ozone demand-free water in said second zone while passing said ozone demand-free water from said second zone into a chilling zone, chilling said ozone demand-free water in said chilling zone, returning the chilled ozone demand-free water to said second zone while continuously adding ozone thereto in said second zone and increasing the ozone in said chilled ozone demand-free water to a specific excess amount, contacting said sludge with said ozone demand-free water containing the specific excess amount of ozone and releasing excess ozone therefrom and oxidizing said oxidizable, hazardous and toxic materials and stabilizable pathogens and microorganisms in a treatment zone, returning ozone demand-free water from said treatment zone to said free zone and recovering treated sludge from said treatment zone from disposal.

11. A method for obtaining ice saturated with ozone, comprising introducing water into a first zone, bubbling ozone into the water in said first zone for a time sufficient to kill substantially all bacteria present in said water and form ozone demand-free water, passing the ozone demand-free water from said first zone to a second zone, bubbling ozone into said ozone demand-free water in said second zone while passing said ozone demand-free water from said second zone into a chilling zone, chilling said ozone demand-free water in said chilling zone, returning the chilled ozone demand-free water to said second zone while continuously adding ozone thereto in said second zone and increasing the ozone in said chilled ozone demand-free water to a specific excess amount, contacting said ozone demand-free water containing the specific excess amount of ozone with pure water in an ice making mechanism whereby said ozone water and said pure water form ozone-saturated ice.

12. Apparatus for obtaining ozone-saturated water, comprising a first container means for holding water, ozone bubbling means connected to said first container means for introducing ozone into water in said first container means, a second container means for holding ozone demand-free water from said first container means, means connecting said first container means with said second container means to pass ozone demand-free water from said first container means to said second container means, means connecting said ozone bubbling means to said second container means, and chilling container means connected to said second container means for receiving ozone demand-free water from said second container means, means connected to said chilling container means and to said second container means for returning chilled ozone demand-free water to said second container means, means for withdrawing the chilled ozone demand-free water containing a specific excess amount of ozone from the second container means.

13. The apparatus according to claim 12 including means for recirculating ozone water into said second container means.

14. Apparatus according to claim 12 wherein a circulating pump is disposed between the second container means and the chilling container means.

15. Apparatus according to claim 12 wherein a water heater is disposed between the second container means and the means for withdrawing said ozone.

16. Apparatus according to claim 12 wherein the first and second container means are stainless steel tanks.

17. Apparatus according to claim 12 wherein the chilling container means is a chiller.

18. Apparatus according to claim 12 wherein the chilling container means is a chilling heat exchanger.

* * * * *